United States Patent [19]

Brunsting et al.

[11] Patent Number: 4,523,841
[45] Date of Patent: Jun. 18, 1985

[54] RADIANT ENERGY RERADIATING FLOW CELL SYSTEM AND METHOD

[75] Inventors: Albert Brunsting, Miramar; Walter R. Hogg, South Miami, both of Fla.

[73] Assignee: Coulter Electronics, Inc., Hialeah, Fla.

[21] Appl. No.: 20,817

[22] Filed: Mar. 15, 1979

[51] Int. Cl.³ .................... G01N 21/47; G01N 21/64
[52] U.S. Cl. .................................. 356/73; 356/340; 356/343
[58] Field of Search .................. 356/73, 337–343, 356/336, 440; 250/574, 578; 340/630

[56] References Cited

U.S. PATENT DOCUMENTS

| | | | |
|---|---|---|---|
| 3,248,551 | 4/1966 | Frommer | 356/441 |
| 3,431,423 | 3/1969 | Keller | 356/338 |
| 3,705,771 | 12/1972 | Friedman et al. | 356/343 |
| 3,819,940 | 6/1974 | Laws | 250/578 |
| 3,850,525 | 11/1974 | Kaye | 356/73 |
| 3,946,239 | 3/1976 | Salzman et al. | 356/39 |
| 4,070,113 | 1/1978 | Frazer et al. | 356/343 |
| 4,070,298 | 1/1978 | Falconer | 356/73 |
| 4,124,302 | 11/1978 | Kuzmin | 356/440 |
| 4,150,360 | 4/1979 | Kopp et al. | 350/162 SF |
| 4,188,543 | 2/1980 | Brunsting et al. | 356/339 |

FOREIGN PATENT DOCUMENTS

| | | | |
|---|---|---|---|
| 1335466 | 10/1973 | United Kingdom | 356/338 |
| 486251 | 4/1976 | U.S.S.R. | 356/338 |

*Primary Examiner*—William H. Punter
*Attorney, Agent, or Firm*—Silverman, Cass & Singer, Ltd.

[57] ABSTRACT

In an apparatus in which particles which may include biological cells are passed through an optical sensing zone to measure their spatial radiant energy distribution for the purpose of identifying and/or characterizing the particles or cells, a structure and method are provided for increasing the usefulness of a geometric configuration of photovoltaic detectors such as a known assembly of generally concentric rings of such detectors usually including some wedge-shaped detectors. These are provided in a generally planar form and the invention provides structure which captures radiant energy in a flow cell of a particular type before projecting the energy to the detector. In particular an ellipsoid, paraboloid, hyperboloid or similar reflector which is symmetrical about its optical axis is utilized first to capture the radiant energy on angles which could include most forward and/or backward angles and all azimuthal angles and then deviating the same to the detector assembly mentioned. By moving the arrangement or assembly of detectors along the optical axis of the reflector the optimum distance is established for obtaining the greatest amount of information sought.

Although the assembly of photovoltaic detectors may thereafter be left in place, it is preferred to substitute for said assembly a second highly economical deviating or reflecting device capable of capturing the radiant energy which would otherwise have fallen on the sensitive plane of the assembly of photovoltaic detectors and deviating the same along a plurality of different spaced paths to independent photodetecting devices.

6 Claims, 7 Drawing Figures

RADIANT ENERGY RERADIATING FLOW CELL SYSTEM AND METHOD

CROSS REFERENCE TO RELATED APPLICATIONS

The basic concept of this invention which comprises the improvement of the usefulness of a known integral planar geometric configuration of photovoltaic detectors whereby it is highly flexible and is rendered capable of measuring most forward or backward scattering angles and in all azimuths is independent of the two applications which are identified below.

In a preferred form of the invention, however, an arrangement is utilized by substitution for the integral planar geometric configuration of photovoltaic detectors which enables the fabrication of a highly effective and economical device without the configuration. This preferred form of the invention utilizes teachings of the following patent applications: "Apparatus and Method for Measuring the Distribution of Radiant Energy Produced in Particle Investigation Systems", Ser. No. 000,439, filed Jan. 2, 1979 and "Apparatus and Method for Measuring Scattering of Light in Particle Detection Systems", Ser. No. 000,438, filed Jan. 2, 1979.

The applicants herein are the applicants in both of the above referred to applications and both of the said applications together with this one are owned by the same assignee.

FIELD AND BACKGROUND OF THE INVENTION

This invention is concerned generally with the measurement of the spatial distribution of radiant energy such as that of reradiated light produced by scattering and fluorescence. More particularly the invention is concerned with the measurement of the energy and direction of light flux or rays produced and reradiated or distributed by particles passing through an optical sensing zone whereby to enable the identification of the particles and/or their characteristics.

One problem with known measurement systems (not including those which are disclosed in the said copending applications) is that they are limited considerably in the range of polar angles that can be measured. For the purposes of this discussion the optical axis of reradiation may be considered the line of the incident light beam projected at a sensing zone where a particle intersects the same. Using conventional definitions, the polar angles are those defined by the angles of the optical axis with lines centered at the sensing zone or point and radiating from that zone, while the azimuthal angles are those measured around the optical axis.

One attempt has been made to evolve an arrangement which can measure multiple angles by means of an integral, planar, geometric configuration of photovoltaic detectors, but the problem with this device is that it can only measure polar reradiating angles from about 1° to somewhat less than 25°. Any attempt to measure the energy distribution in most polar angles in the forward (0° to 90°) and all angles in the backward direction relative to the sensing or scattering zone and the incident light direction including all azimuthal angles, fails because the sensitive area of the device is too small. This is because all of the photovoltaic elements which "see" the energy must be mounted on the same plane within the available space which is limited. Accordingly the utility of the device is limited.

The particular device which is referred to is in the form of a concentric ring and wedge photovoltaic detector. It is described in considerable detail in U.S. Pat. No. 4,070,113 and in two articles entitled "Light-Scattering Patterns of Isolated Oligodendroglia" by R. A. Meyer, et al in *The Journal of Histochemistry and Cytochemistry*, Vol. 22, No. 7, pp 594–597, 1974 and a second article entitled "Gynecological Specimen Analysis by Multiangle Light Scattering in a Flow System" by G. C. Salzman et al in the same journal, Vol. 24, No. 1, pp 308–314, 1976. In these articles reference is made to the same or a similar detector device which is commercially available and which is identified as a Recognition Systems, Inc. detector (RSI).

The configuration of detectors which has been mentioned above will be referred to hereinafter as a planar configuration of detectors. As known at this time the one mentioned in the above references is expensive, difficult to manufacture, delicate, inefficient and slow-acting because of its relatively large area considering the number of detectors which it carries. The inefficient optical design results in a poor signal to noise ratio.

Notwithstanding these disadvantages, such a configuration and in general any radiant-to-electrical energy transducers configured in a geometric assemblage which is planar are and can be useful within the field they occupy, but according to the invention herein, this usefulness is materially increased. The planar configuration of detectors at the minimum can serve the purpose of helping to find a location at which some desired set of polar reradiating angles are the optimum for a given optical system and for a particular family or type of particles being studied.

Once an optimum position has been achieved in a given system, the planar configuration of photovoltaic detectors may be removed from the system and a more economical device substituted therefor, this latter device comprising a composite deviating lens or reflector which is formed of a large number of elements such as prisms each oriented to deviate or reflect a certain geometric portion of the reradiated energy area being studied to different and spaced apart commonly available and highly economical photodetecting devices such as small photocells. The measurements from all of the photocells give the information desired.

Prior art patents which may be of interest are: U.K. Pat. No. 137,637 of 1920 to Pollard and Frommer U.S. Pat. No. 3,248,551.

SUMMARY OF THE INVENTION

A system for measuring reradiated radiant energy which has been scattered or reradiated by fluorescence which includes a flow cell in which a particle or a biological cell is passed through a sensing zone which additionally comprises the focus of a reflector on the interior thereof. The reflector may comprise a concave geometric shape symmetrical around its axis and adapted to capture reradiated light (e.g. scattered or fluorescent) from wide and narrow polar angles and all azimuthal angles and to project the same out of the reflector. The reflector is a shape of revolution of a geometric law about its optical axis. As used herein light means any electromagnetic radiation which is capable of being detected by transducers of the type utilized in this art.

Means are provided for bringing the particles, cells or scatterers as they are often called herein, into the reflector as for example in a liquid flow, the reflector interior being enclosed and having a compatible liquid sealed therein.

The rays of light projected by the reflector may be either focussed or directed without focussing onto an integral, planar configuration of photovoltaic detectors of a construction known in the prior art thereby increasing the usefulness of that device.

One aspect of the invention provides for the configuration of detectors to be located at a place along the axis of the geometric reflector which provides the most favorable information in the particle system being investigated. Another aspect has the configuration movable to find such a place. A third aspect teaches that once the best location has been found, a different structure is substituted for the configuration which comprises a composite lens or a composite reflector which captures the rays of reradiated light and either deviates them or reflects them in a plurality of different directions relative to the axis of the geometric reflector. An individual photocell of economical construction is then located to intercept each respective one of these rays and the investigation is carried out by monitoring all of the photocells.

The apparatus may be used for fluorescent light measurements by using filters to separate scattered and fluorescent light produced at the same sensing zone.

DESCRIPTION OF THE PREFERRED EMBODIMENTS

Basically the invention comprises a flow cell in which there are means for collecting radiant energy around the first focal zone where a particle or other small body, hereinafter called a scatterer, passes through a beam of light and causes secondary radiation from said particle; the collecting means causes a reflection of said secondary radiant energy to a second focal zone and to detector means capable of responding to at least one of several multiple angles of projected radiation. In one form, the detector means comprise a known concentric ring photovoltaic detector and it is adjusted along an axis which passes through both the first and second focal zone. The optimum position for detecting the desired information from the scatterer is used. In an improved form, the detector means comprise a fresnel prismatic lens or other optical element of a composite nature which deviates or reflects the incident radiant energy flux in accordance with a plurality of different geometric areas to different, spaced apart, independent, small, photodetector devices in a highly economical manner.

Other forms of the invention provide for back scattering.

Figure 1:
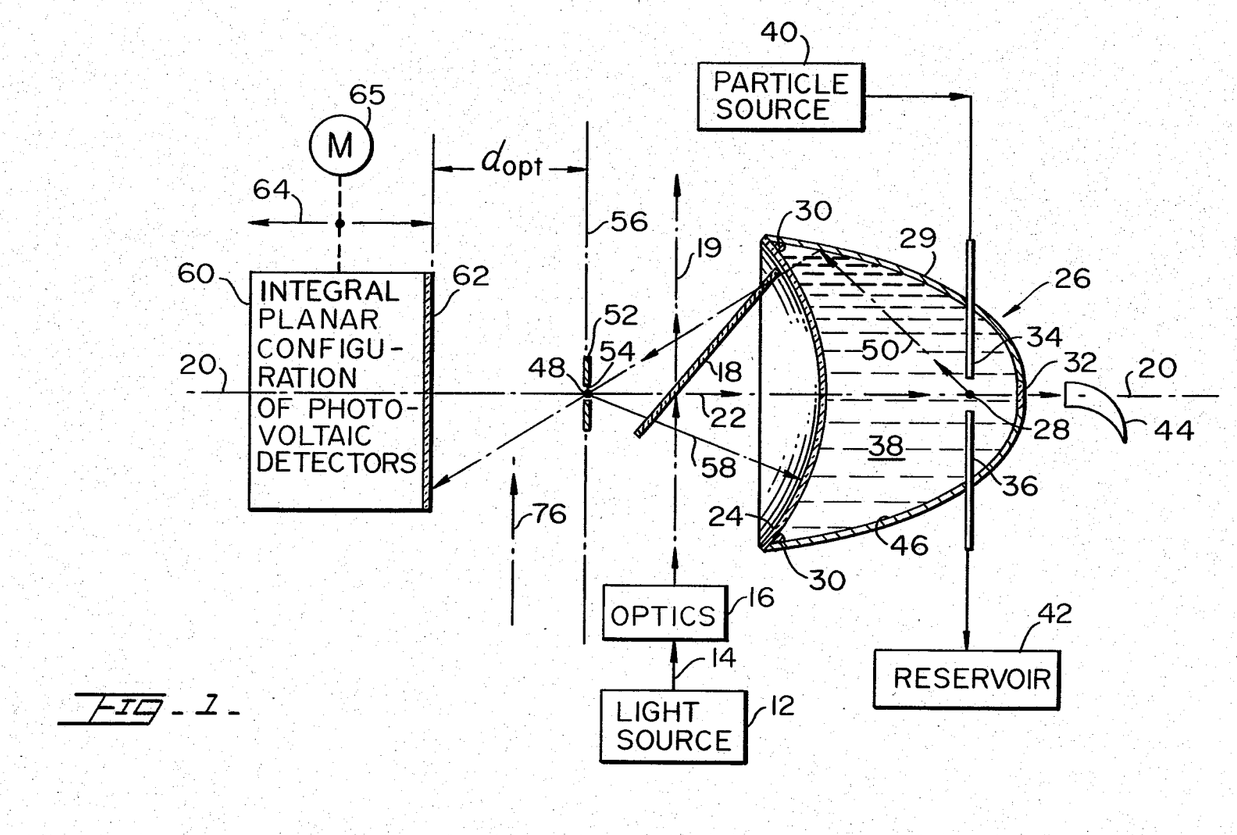
FIG. 1 is a diagrammatic view of a light reradiating flow cell system constructed in accordance with the invention and using as an element thereof an integral planar configuration of photovoltaic detectors.

In FIG. 1 there is illustrated a flow cell system in which there is a source of light 12 which projects a beam 14 through a suitable optical train which is called optics 16 to a partial reflector 18 on the optical axis 20. The partial reflector or beam splitter projects the incident light along axis 20 at a reduced intensity, now designated 22, through the spherical closure window 24 of the flow cell 26 to the sensing zone 28. Transmitted light passes undeflected through the beam splitter 18 as shown at 19 to other uses.

The flow cell 26 can be constructed using conventional techniques for sealing and the like and it comprises a reflector 29 that is a portion of an ellipsoid, having the window 24 sealed to its front and open end as at 30, having a rear window 32, an entering conduit 34 and a discharging conduit 36. The cell 26 is filled with a fluid 38 that is compatible with the liquid which carries the particles and has the same index of refraction as that liquid. The particle source 40 moves the scatterers in the fluid mentioned to the entering cnduit 34 from which they pass through the sensing zone 28 into the entrance of the discharging conduit 36 and pass into the reservoir 42. By techniques known as sheath flow the fluid with scatterers may be caused to pass in a straight path across the sensing zone 28 and be discharged.

The beam of light 22 intersects the flow of scatterers at the sensing zone 28. That light not scattered plus that light scattered into small polar angles in the forward directions passes on through the window 32 into the light dump 44. Instead of such light dump there could be another detecting system as disclosed in said copending applications.

The sensing zone is chosen to be centered in the region of the first focal point of the ellipsoid of which the reflector 29 is a part. The interior surface 46 of the reflector 29 is polished or mirrored and all light or radiant energy which originates at its focal point 28 will be reflected from the surface 46 to the second focal point 48 of the ellipsoid of which the reflector 29 is a part. A typical ray of light is designated 50 and its path may be traced from the first focal point 28 upward and to the left to reflect from the surface 46 and then directly to the second focal point 48.

All of the reflected rays of the reradiated energy from the reflector 29 are focused at the focal point 48 and will thereafter (to the left of the point 48) diverge. An aperture 54, through which the radiant energy beams may pass and which eliminates most stray light, is located in opaque barrier 52 and at the focal point 48. The plane of the opaque barrier 52 is designated 56, this being a plane which is normal to the axis 20 and the beam 22. It will be noted that the radius 58 of the spherical transparent window 24 which may be of glass is centered at the focal point 48 to eliminate any refractive bending in the beam 50 or any others which emerge from the reflector 29.

At a distance d from the plane 56 there is provided the planar configuration of detectors 60 which has previously been mentioned. The planar face 62 of the configuration 60 has the photosensitive elements and this face 62 is parallel with the plane 56. Accordingly its several rings and wedges, if it has such wedges, will respond to the portions of the radiant energy which fall upon them, respectively. As will be noted, the angles which can be captured by the reflector surface 46 can be as large as 140° for example. By itself, as previously mentioned, a device such as 60 has only been capable of collecting scattering angles to a maximum of 25° or so. Thus, the detector 60 has had its utility increased. By virtue of the invention herein it is made capable of responding to many more scattering angles and providing much more information than if it received the scattering light directly from the sensing zone 28 with no ellipsoidal reflector in place.

By moving the configuration 69 right and left through the medium of a motor 65 or the like as indicated by the double arrow 64 the optimum position can be obtained for determining the information desired. This, of course will depend upon the type of scatterers, what information is desired of them, etc. Actually, by moving the configuration of detectors 60 over a range of the dimension d information can be obtained from a variety of locations, keeping in mind, of course, that the largest scattering angle falling on the detector will decrease as the distance d is increased.

Once a given course of investigation is to be followed and the optimum $d_{opt}$ has been ascertained and the corresponding scattering or reradiating angles have been calculated, instead of leaving the planar configuration of detectors 60 in place, fresnel lens elements 66 and 69 (FIG. 2) made up of portions of prismatic wedges or segments or rings oriented in different directions relative to the axis 20 and/or tilted relative to said axis 20 may be substituted for the device 60. The fresnel prismatic lens deviates the converging rays of radiant energy to different spaced apart photocells such as shown at 68, 70, 72 and 74. The latter are small, sensitive, economical elements easily obtained commercially and easily replaced. They can be separated by distances to prevent interference between them, often referred to as "cross-talk". The rays of radiant energy projected from the reflector surface 46 (FIG 1) are focussed again at the second focal point 48 of the aperture 54 (FIG. 2) and the typical ray 50 is directed at the fresnel prismatic lens 66. Just in front of this lens 66 a focussing lens 69 has been located for the purpose of converging the rays from the reflector 29 before they impinge on the prismatic elements of the lens 66. The focussing lens 69 can be a conventional ground or molded lens or could be a fresnel focussing lens as illustrated.

Figure 2:
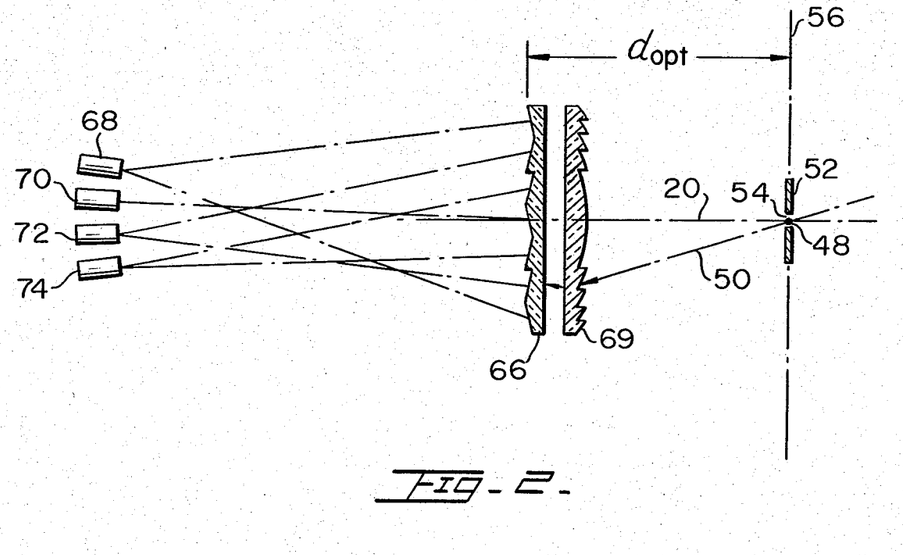
FIG. 2 is a fragmentary view of the left hand portion of the system of FIG. 1 but showing how a fresnel lens and individual photocells are substituted for the configuration of photovoltaic detectors of FIG. 1.

The concept of utilizing the type of prismatic lens 66 which has been described in connection with FIG. 2 and the details and benefits thereof are disclosed in the copending applications.

Thus, an instrument can be built using the planar configuration 60 in which the detector is moved by some mechanical means 65 or even manually to provide flexibility; an instrument can be built in which the configuration 60 has been fixed in place after adjustment in the factory to a particular distance d for a specific purpose; an instrument can be built of the latter type in which a very economical fresnel lens which has the equivalent function of the optimum arrangement has been substituted for the configuration 60 after the best location $d_{opt}$ has been determined.

The exact mechanical construction of the components of the system 10 may be left to those skilled in the art who would understand that the structure for assembling the flow cell 26 and its parts must provide for filling, bubble relief, etc.

It should be appreciated that the increased utility of the integral planar configuration of detectors 60 over that for which it is at the present used comes about by virtue of the fact that in the invention, each ring of the device 60 can correspond to a large range of scattering angles, certainly larger than the range of angles that is represented by the present conventional way of using the said device 60.

Back scattering angles can be measured in the apparatus 10 simply by disposing the light dump 44 below the mirror 18 at the location occupied by the optics 16 and light source 12 and by disposing the optics 16 and light source 12 where the light dump 44 is located in FIG. 1. In this way, the beam 22 will have its arrows reversed, light coming in by way of the window 32 and passing from right to left as viewed in FIG. 1. In all other respects the system 10 will not be altered.

The system admits of variations and uses in addition to the one described above without departing from the basic concept of the invention. For example, the location of the light source 12, optics 16 and mirror 18 need not be where shown but could be at a location between the plane 56 and the detector 62. The location is indicated at 76 in FIG. 1, this being the line along which the beam 14 would be projected toward the previous position of the mirror 18. The mirror 18 need not be fully reflecting but could be semi-transparent. Fluorescent light reradiation can be measured with the apparatus 10 if slightly modified as explained hereinafter.

Figure 3:
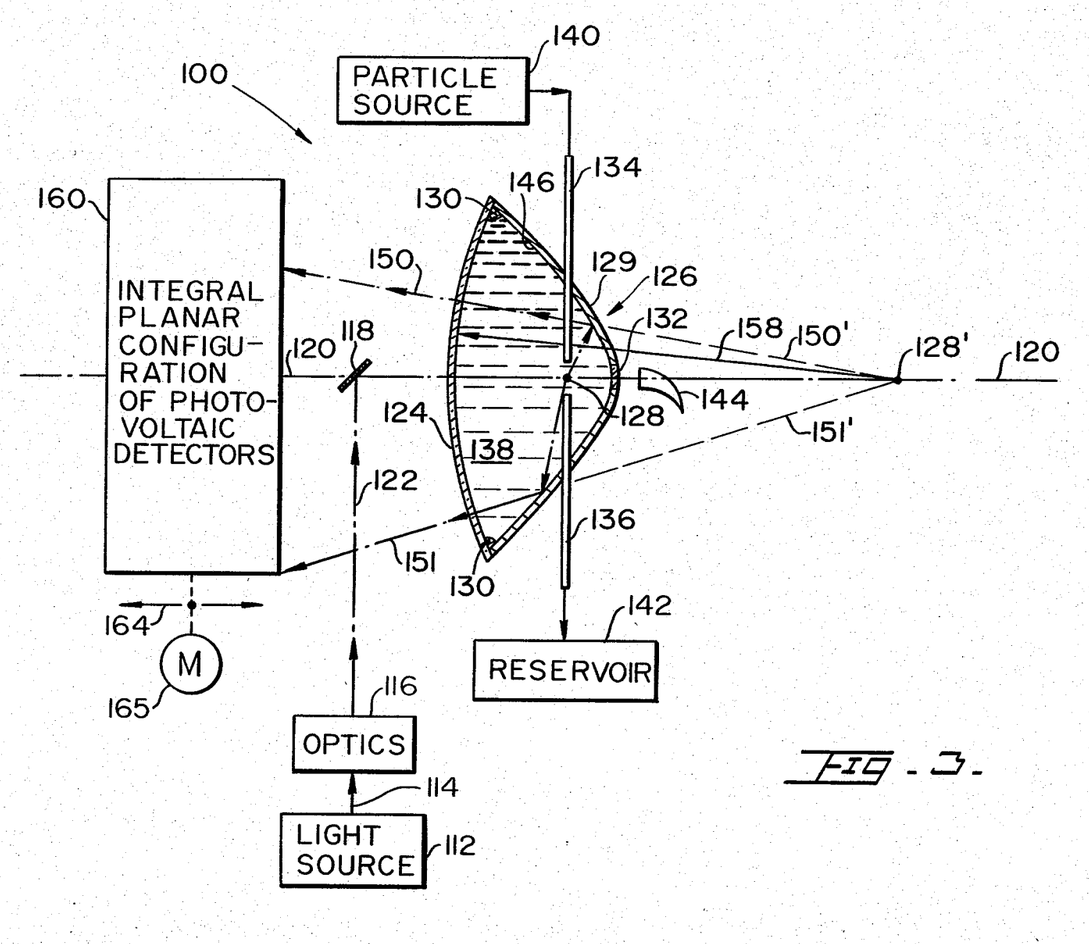
FIG. 3 is a view similar to that of FIG. 1 but illustrating a form of the invention using a hyperboloidal reflector instead of an ellipsoidal reflector for certain specific measurements.

In FIG. 3 there is illustrated a system 100 in which the object of the apparatus is to investigate scattering angles closer to the forward direction than can be obtained through the use of the ellipsoidal reflector 29 of FIG. 1. The flow cell 126 in this instance is comprised of a hyperboloidal reflector 129 whose axis is designated 120 and having a first focal point 128 and its second or virtual focal point at 128'. As in the case of the cell 26, the interior of the cell 126 is provided with a fluid 138 which may be held in place by a glass or other material transparent spherical closure 124 whose radius of curvature 158 is centered on the virtual focal point 128'. Particle source 140 provides the scatterers in a liquid which flows into the interior of the cell 126 by way of the entrance conduit 134 through the sensing zone-focal point 128 and out by way of the discharge conduit 136 to the reservoir 142.

Light from the source 112 is directed as a beam 114 to the beam shaping optics 116 and thence as the beam 122 to the folding mirror 118 on the axis 120 through the front of the closure 124 to the sensing zone-focal point 128 and out the window 132 to the beam dump 144. Typical light rays or fluxes resulting from the scattering are shown at 150 and 151 and it will be noted that these diverge, rather than converge, giving information on the type of polar angles mentioned above, that is, smaller forward angles.

These beams, as the others which are not shown, are captured directly in FIG. 3 by the configuration of detectors 160 which can be moved in the direction of the arrow 164 by a motor such as 165 or by manual means to find the best location along the axis 120 relative to the cell 126. When the optimum distance has been located, collecting optics, a fresnel lens and individual photocells may be substituted for the device 160. It will be noted that the direction along which the beams of scattered light 150 and 151 extend are extensions of lines 150' and 151' respectively from the virtual focal point 128'. In this case no stray-light suppressing aperture 54 is used.

Figure 4:
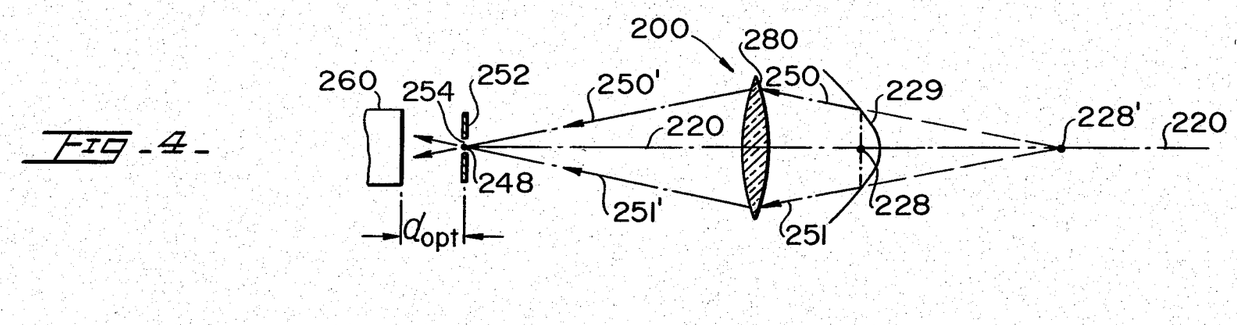
FIG. 4 is a simplified diagram of a modified form of the invention illustrated in FIG. 3.

In the system 200 of FIG. 4, the light flux or rays emerging from the hyperboloidal reflector 229 are not used in their diverging form but are focussed so that they may be passed through an aperture for suppressing the stray light before being measured. Thus, the light rays 250 and 251 which are typical of scattered light reradiated from the sensing zone-focal point 228 are captured by the lens 280, focussed on the aperture 254 provided by the opaque barrier or iris 252 at the focal point 248 and then are brought to the device 260 which is the same integral geometric configuration of photovoltaic detectors which was described above. One good choice of the distance of the lens 280 from the focal point 228' on the axis 220 is twice the focal length of the lens. Then the aperture 254 will be located at the focal point 248, which is twice the focal length of the lens 280 from the lens.

Again, as in this structure, it is feasible to have the device 260 movable, to adjust it for optimum distance $d_{opt}$ from the aperture 254 and to substitute collection optics and a fresnel lens or a composite mirror in its place.

Instead of the lens 66, in which the light or radiant energy passes through the deviating means, it is feasible to use a composite mirror of multiple reflecting surfaces which receives the beams of light and reflects them to a plurality of spaced individual locations so that the separate photocells may be located thereat.

Figure 6:
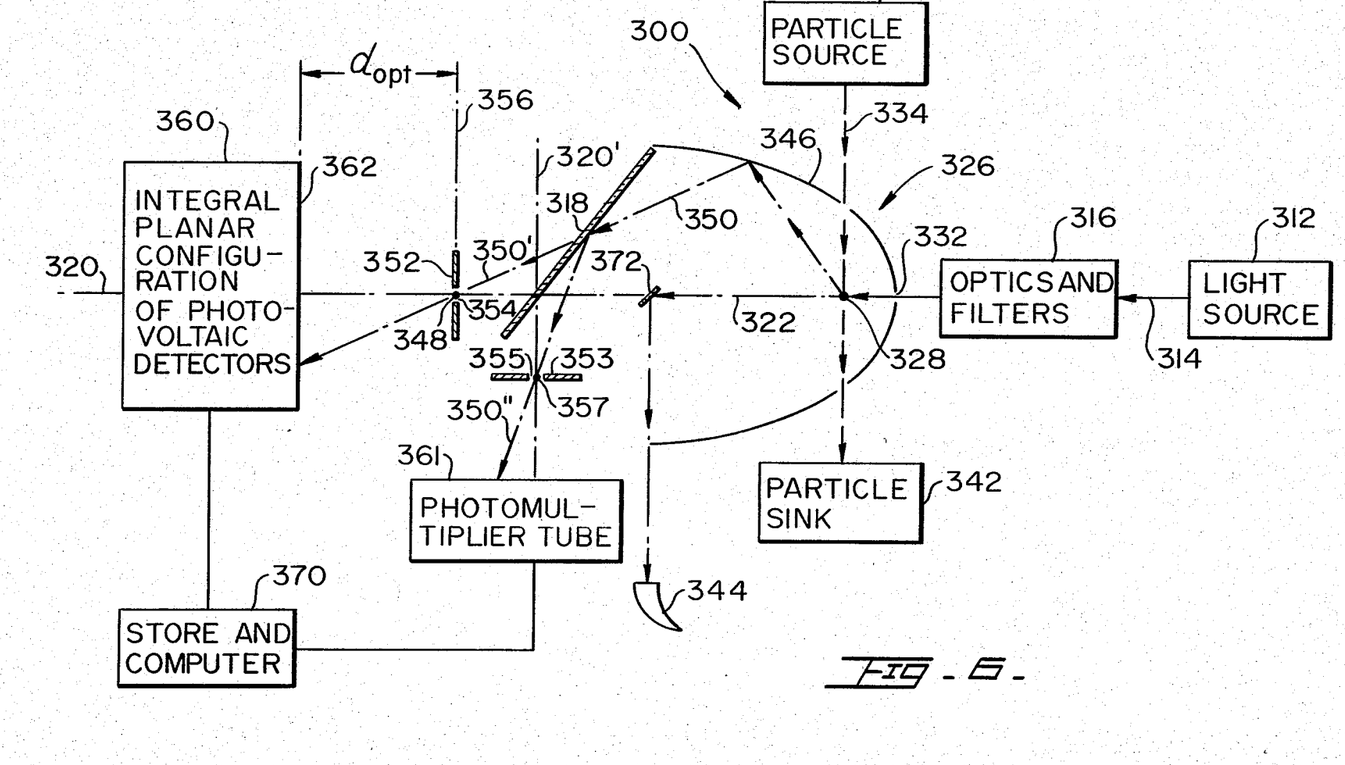
FIG. 6 is a simplified diagram of a form of the invention for additionally measuring fluorescence.

In FIG. 6 there is illustrated the application of the invention to a system 300 in which fluorescent reradiation is measured in addition to reradiation by scattering. In this case there is a flow cell 326 which is basically built out of an ellipsoidal reflector 346 but of course this could be any configuration of reflector of the types explained herein. The reflector 346 has a window 332 through which the light beam 322 from the light source 312 and optics 316 enters. The light source 312 could be a suitable laser and the beam 314 therefrom is applied to beam-shaping optics 316.

The beam 322 passes through the first focal point 328 of the reflector 346 where it encounters particles or cells which are entering the reflector along the path 334 from the particle source 340. At the first focal point 328 light will be reradiated in accordance with the character of the particle and this light will be reflected from the reflector 346 towards the second focal point 348 which lies in the plane 356 normal to the optical axis 320. A typical ray is indicated at 350 and this ray is shown striking the interior of the reflector 346 at the top thereof in the view and being deflected toward a mirror 318 which intercepts the ray.

The mirror 318 which is here chosen is a dichroic element in that light is transmitted or reflected according to the wavelength of that light. The ray 350 includes components which are fluorescent and other components of visible light. The dichroic mirror 318 is constructed to have substantially no effect upon light of the laser wavelength and hence those components of the beam 350 pass through the mirror 318 without deflection albeit somewhat diminished. These move toward the second focal point 348 as the ray 350' and impinge on the sensitive surface 362 of the integral planar configuration of photovoltaic detectors 360 which is the equivalent of the prior art device 60 previously described.

The direct rays of light at 322 pass into a light dump 344 after being reflected by small mirror 372.

The light rays which focus at the second focal point 348 are purified by the opaque barrier or iris 352 which lies in the plane 356 that is normal to the axis 320 and passes through the second focal point 348. Light passes the barrier 352 by way of a center aperture 354 in the barrier. Again the distance d between the plane 356 and the face 362 can be adjusted by suitable means to be optimum and when this is achieved a collector and fresnel prism element with separate photodetectors substituted therefor as explained.

Those components of the ray 350 which have wavelengths to which the action of the dichroic mirror 318 will become effective are reflected by the mirror as the ray 350" to focus at the point 357 along the axis 320' which axis is shown perpendicular to the axis 320. At the focal point 357 there is a purifying opaque barrier 353 with an aperture 355 so that the reflected rays such as 350 will pass through the barrier. It is there intercepted by a suitable transducer such as a photomultiplier tube or element 361 so that measurements can be made and compared against known information to identify or characterize the particle. The combined information from the device 360 (or any system or fresnel lens and photodetectors substituted therefor) and the transducer 361 can be channeled to a computer 370 where previously known information is stored and against which the new information can be compared.

The rays such as 350' which pass through the dichroic mirror 318 will have less radiant energy than the original rays 350. Accordingly it is desired for maximum information to have as sensitive a detector at the position of the device 360 as feasible. The copending invention teaches how this can be done by substituting the prismatic fresnel lens system and its detectors for the low sensitivity device 360.

Figure 7:
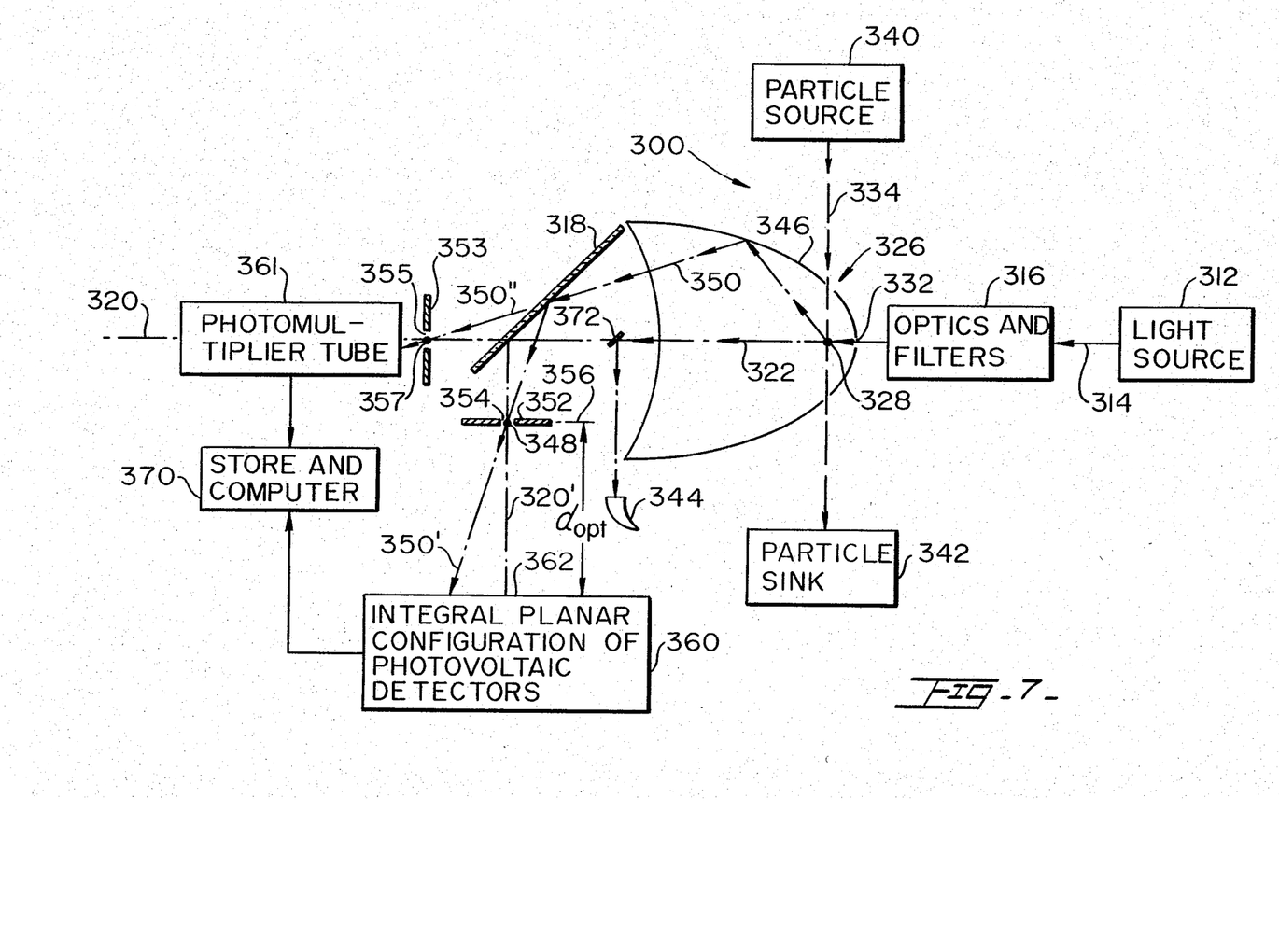
FIG. 7 is a simplified diagram of another form of the invention which is the same as FIG. 6 but symmetrically reversed about a dichroic mirror in order to permit the use of commercially more available mirrors.

FIG. 6 has been included to illustrate apparatus based on the principle of collecting scattered and fluorescent light separately through the use of a dichroic mirror. To facilitate explanation, the version in which the scattered light is transmitted and the fluorescent light is reflected is shown. As a practical matter, however, due to manufacturing problems of the dichroic mirror, the inverse arrangement, in which fluorescent light is transmitted while the scattered light is reflected, is actually the preferred embodiment. This latter is illustrated in FIG. 7 and is identical to FIG. 6 except for the transposition of the respective elements.

In the course of the explanations given herein and in the claims, reference is made to focal points and to specific geometric configurations of reflectors such as ellipsoids, paraboloids, etc. The manufacture of instruments which embody and use all of the benefits and advantages of the invention would call for providing components which are formed with precision; however, for economy the configurations are certainly capable of being formed as approximations. Thus when specific configurations are mentioned it should be taken to mean that in addition to the precise geometric configurations substantial and/or approximate approaches to such configurations are intended to be included herein. Focal points may not always be precisely a point but may be a sort of zone but will still give the desired results. Reference to two focal points in the discussion and claims is not intended to exclude paraboloidal reflectors inasmuch as the second focal point thereof is considered to be at infinity.

Figure 5:
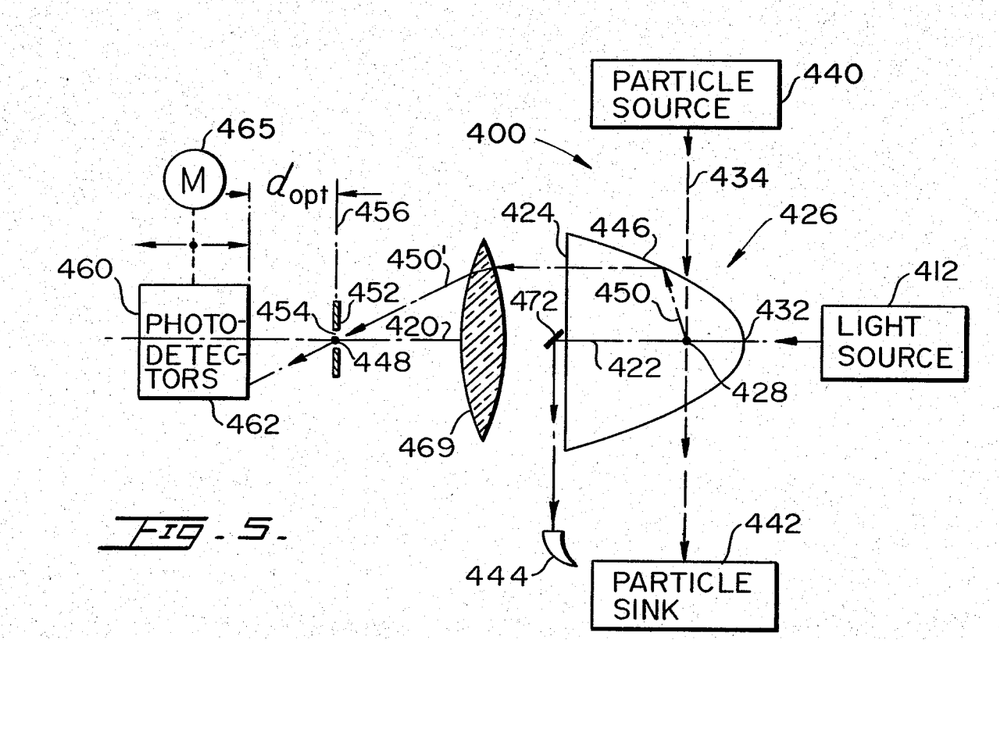
FIG. 5 is a simplified diagram of another form of the invention using a paraboloid.

Such a paraboloidal reflector is illustrated in connection with the apparatus 400 of FIG. 5. This apparatus includes a flow cell 426 which has a parabolic reflector 446 whose front opening is closed off by a suitable closure 424 which is planar because the reradiated radiant energy which emerges from the reflector 446 emanates along lines which are parallel to the optical axis 420. The light source 412 in this instance is behind the reflector 446 as shown and it projects a beam of incident radiant energy along the path 422 toward the folding mirror and onto the light dump 444, this beam of incident radiant energy passing through the sensing zone which coincides with the focal point 428 of the paraboloid 446. Particles originating at the source 440 move along the path to the focal point 428 and at that point which comprises the sensing zone they intercept the beam 422 and reradiate some of the radiant energy of said beam. The rays move outward of the focal point 428 as for example along the line 450, engage the inner surface of the reflector 446 and thereafter are projected parallel to the axis 420, as stated above, toward what may be considered the second focal point of the reflector 446 at infinity.

In order to utilize the benefits of the invention, the groups of rays emerging from the front of the reflector 446 are captured by a focussing lens 469 which may be of conventional construction or fresnel construction and diverted along the lines such as 450' to another focal point at 448. This focal point is located relative to the reflector 446 in accordance with the optical specifications of the lens 469 (or a lens system used in lieu thereof) rather than as a result of the geometric law which defines the paraboloid.

At this focal point 448 there is an opaque barrier or iris 452 having a central aperture 454, these both lying on a plane 456 which is normal to the axis 420. At a distance d from the plane 456 there is located a measuring device which comprises an integral planar configuration of photovoltaic detectors 460 whose sensitive surface is in the front plane thereof at 462. The ray groups 450' emerging from the reflector 446 and focussed at the focal point 448 diverge after being purified of stray light at the focal point by the barrier 452 and impinge against the sensitive surface 462 of the measuring device 460. It will be recognized that this measuring device is the same as those which have been referred to herein and identified as 60, 160, 260 and 360.

Again in this case, the measuring device 460 may be moved back and forth parallel to the axis 420 but without changing its disposition relative to the axis to vary the distance d. Once the optimum distance and hence the optimum polar angles have been determined, the known measuring device 460 may be removed and the measuring devices which are disclosed in the copending applications for increased sensitivity and better data may be substituted for collecting light at these angles.

Many other variations are capable of being made without departing from the spirit or scope of the invention as defined in the appended claims.

What is desired to secure by Letters Patent of the United States is:

1. A method of measuring the directional distributional properties of the radiant energy reradiated from a particle for characterization or the like of said particle and using a known integral configuration of photovoltaic detectors having a sensitive front planar surface which method comprises:
    A. Passing the particle through a sensing zone located on the interior of a concave reflector whose configuration is substantially defined by a geometric law, the reflector being symmetrical about an optical axis and having a first focal point also defined by said geometric law, the sensing zone being at said first focal point,
    B. directing a beam of incident radiant energy along said axis to said sensing zone,
    C. intercepting the radiant energy which has been reradiated by said particle and emerging from the front or said reflector at said planar surface,
    D. adjusting the integral configuration along said axis while maintaining its disposition relative to the axis in order to modify the response of said photovoltaic detectors due to said reradiated radiant energy from said particle, and thereafter
    E. removing the integral configuration and substituting therefor a composite optical member having the property of separating the received reradiated energy from said particles into plural individual ray groups and directing said ray groups along an equivalent plural number of respective paths, each group having a different direction relative to one another and a direction divergent from the said axis, and measuring the said individual ray groups separately by respective interception of said plural paths.

2. The method as claimed in claim 1 in which the separation is effected by deviation in transmission through said composite optical member.

3. The method as claimed in claim 1 in which the separation is effected by deviation from said composite optical member.

4. A method of measuring the directional distributional properties of the radiant energy reradiated from a particle for characterization or the like of said particle and using a known integral configuration of photovoltaic detectors having a sensitive front planar surface which method comprises:
    A. Passing the particle through a sensing zone located on the interior of a concave reflector whose configuration is substantially defined by the geometric law for an ellipsoid, the reflector being symmetrical about an optical axis and having a first focal point also defined by said geometric law, the sensing zone being at said first focal point,
    B. directing a beam of incident radiant energy along said axis to said sensing zone,
    C. passing the reradiated radiant energy from said particles through an aperture for the suppression of stray light at the second focal point of said ellipsoid before intercepting the same,
    D. intercepting the radiant energy which has been reradiated by said particle and emerging from the front of said reflector at said planar surface,
    E. adjusting the integral configuration along the axis while maintaining its disposition relative to the axis in order to modify the response of said photovoltaic detectors due to said reradiant radiant energy from said particle, and thereafter
    F. removing the integral configuration and substituting therefor a composite optical member having the property of separating the received reradiated radiant energy into plural individual ray groups and directing said ray groups along an equivalent plural number of respective paths, each having a different direction relative to one another and a direction divergent from the said axis, and measuring the said individual ray groups separately by respective interception of said plural paths.

5. The method as claimed in claim 4 in which the beam of incident radiant energy is directed from the rear of the reflector to said sensing zone whereby to provide primarily information on reradiation directed initially mostly backwards.

6. The method as claimed in claim 4 in which the beam of incident radiant energy is directed from the front of the reflector to said sensing zone whereby to provide primarily information on reradiation directed initially forwards.

* * * * *